United States Patent [19]

Hammer

[11] Patent Number: 5,355,214
[45] Date of Patent: Oct. 11, 1994

[54] FLOW CONTROL DEVICE

[75] Inventor: Michael R. Hammer, Melbourne, Australia

[73] Assignee: Varian Associates, Inc., Palo Alto, Calif.

[21] Appl. No.: 751,279

[22] Filed: Aug. 29, 1991

[30] Foreign Application Priority Data

Aug. 31, 1990 [AU] Australia .............................. PK2064

[51] Int. Cl.⁵ .......................... G01J 3/30; G01N 21/72
[52] U.S. Cl. .................................... 356/315; 356/316
[58] Field of Search ............................ 356/315, 316; 251/129.05, 129.2

[56] References Cited

U.S. PATENT DOCUMENTS

| | | | |
|---|---|---|---|
| 3,926,209 | 12/1975 | Sodal et al. | 137/487.5 |
| 4,201,913 | 5/1980 | Bursack et al. | 250/288 |
| 4,220,413 | 9/1980 | Targowski | 356/315 |
| 4,373,549 | 2/1983 | Nalepa et al. | 137/487.5 |
| 4,640,677 | 2/1987 | Huber | 431/89 |
| 4,669,660 | 6/1987 | Weber et al. | 239/102.2 |
| 4,681,530 | 7/1987 | Huber | 431/89 |
| 4,858,103 | 8/1989 | Takeuchi et al. | 251/129.05 |

FOREIGN PATENT DOCUMENTS

| | | |
|---|---|---|
| 144548 | 6/1985 | European Pat. Off. |
| 0064438 | 3/1990 | Japan ................................ 356/315 |
| 452663 | 12/1987 | Sweden . |

OTHER PUBLICATIONS

Colaneri, "Solenoid Valve Basics," Instruments and Control Systems, vol. 52, #8, Aug. 1979.

*Primary Examiner*—Vincent P. McGraw
*Assistant Examiner*—K. P. Hantis
*Attorney, Agent, or Firm*—Gerald M. Fisher; Edward H. Berkowitz

[57] ABSTRACT

A method and means for accurately regulating the rate of flow of supply gas to the burner or torch of a spectrometer. The flow rate is controlled by a valve having a closure member which is movable between a position at which it provides maximum obstruction to gas flow, and a position at which it provides minimum such obstruction. The closure member movement is controlled by a pulsed electrical signal so that the closure member moves rapidly and repeatedly between each of the two positions. Gas flow rate through the valve is therefore dependent upon the aggregate of the times the closure member spends in either of the two positions referred to, and that flow rate is changed by varying the frequency and/or pulse duration of the pulsed signal.

8 Claims, 3 Drawing Sheets

FLOW CONTROL DEVICE

This invention relates to the method and means for controlling the rate of flow of supply gas to the burner or torch of a spectrometer. Examples of such supply gases are fuel gases and oxidising agents as used in atomic absorption spectroscopy, and plasma and auxiliary gases as used in inductively coupled plasma spectroscopy. It will be convenient to hereinafter describe the invention with particular reference to an atomic absorption (AA) spectrometer, but the invention could be used with other forms of spectrometers such as inductively coupled plasma emission spectrometers and inductively coupled plasma mass spectrometers.

The operation of AA spectrometers is such that the flow rates of the gases supplied to the burner need to be closely controlled, and it is important that the means for changing the flow rate operates rapidly and reproducably so, in order that the results obtained from the AA spectrometer are accurate.

One commercially available prior art system employs a constant gas pressure across an orifice and control of gas flow is achieved by varying the size of the orifice. This is conveniently done by employing a needle valve, the position of the needle being varied using a stepper motor. A pressure regulator upstream of the valve ensures the pressure across the needle valve remains constant. Because the relationship between flow and needle valve shaft angle is quite uncertain both within any one valve and from one valve to another, it is not possible to obtain satisfactory performance with an open loop control configuration. Accordingly a separate transducer is used to measure the actual flow downstream of the needle valve and this information is combined with the needle position information in a closed loop arrangement in a control facility. The control facility, which is conveniently a microprocessor, is part of this control loop, and must respond in real time to control the system.

The closed loop system has a slow response time since the stepper motor takes a long time to position the needle valve and overall loop stability requirements impose still further speed limitations. This slow rate of response is undesirable in rapid sequential types of instrument, and can also necessitate the addition of further complications in the pneumatic circuitry, such as the inclusion of means to allow rapid increase in fuel gas when changing oxidizing agent.

The incorporation of the microprocessor in the control loop places a significant real time load on the processor, reducing time available for other functions, and renders the system susceptible to software malfunctions.

Prior art flow control systems tend to be costly because of the large number, and expense, of components required. Clearly the stepper motors conventionally used, and the needle valves themselves, are expensive items, and since two separate valves are used, one for each gas supply, the valves and controls add significantly to the overall cost of the AA spectrometer.

It is an object of the invention to provide a method of controlling gas flow in a spectrometer, the use of which will at least ameliorate the above problems. A further object is to provide a flow control device for use in a spectrometer, which utilises the method and is able to accurately control the rate of fluid flow through a conduit without feedback and able to establish or change a flow very rapidly. Another object of the invention is to provide a flow control device which is easily controllable by electrical or electronic means. Still another object of the invention is to provide a spectrometer having an accurately controllable supply gas system.

In accordance with one aspect of the present invention, there is provided a method of controlling the flow of supply gas within a spectrometer including the steps of passing the gas through an electrically operable device which is switchable between a maximum flow condition and a minimum flow condition, connecting a pulsed electrical signal to said device so as to thereby cause the device to switch repeatedly and in a controlled manner between the two said flow conditions, and varying the pattern of said signal as required to vary the aggregate of the times the device resides in one or each of said flow conditions during a given time period and thereby change the flow rate of said gas through the device.

In accordance with another aspect of the invention there is provided a spectrometer supply gas valve including a passage for transfer of supply gas from one location to another, a closure member movable between a first position at which it provides maximum obstruction to said gas transfer and a second position at which it provides minimum said obstruction, and control means which is responsive to a pulsed electrical signal to cause said closure member to switch repeatedly and in a controlled manner between said two positions, the arrangement being such that the flow rate of gas through said passage is determined by the aggregate of the times the closure member resides in one or each of said positions during a given time period, and said flow rate is changed by varying the pattern of said signal.

In accordance with still another aspect of the invention, there is provided a spectrometer including, a passage for transferring supply gas from one location to another, a valve for controlling the rate of gas flow through said passage and having a closure member movable between a first position at which it provides maximum obstruction to said gas transfer and a second position at which it provides minimum said obstruction, control means which is operative to cause said closure member to switch repeatedly and in a controlled manner between said two positions so that the flow rate of gas through said passage is determined by the aggregate of the times the closure member resides in one or each of said positions during a given time period, a source of a pulsed electrical signal connectable to said control means so as to render said control means operative, and modulating means which is operable to change the pattern of said signal and thereby change said gas flow rate.

Reference throughout this specification to residence of the device or the closure means in a flow condition is not to be understood as necessarily meaning that the device or closure member lingers for a significant period of time in either flow condition during a switching cycle. In some circumstances, the manner of switching may be such that the device commences to move out of a flow condition immediately, or almost immediately, that flow condition is adopted. Switching is controlled by the pattern of the pulsed signal, and that pattern is determined by the duration of each pulse and the pulse frequency during the relevant time period. A variation in the pattern of the signal may involve a change in the pulse duration, or frequency, or both.

A method as described above controls, in an accurate manner, the percentage of a given time period during which the flow control device or closure means is in each of the two flow conditions. By varying the aggregate of the times during which the device or closure member is in either or both of those conditions over any given time period, it is possible to accurately establish a particular flow rate through the device and any associated conduit.

It is possible that some obstruction to flow will exist in the maximum flow condition, and the minimum flow condition may or may not be a no-flow condition.

In a preferred arrangement, the closure means referred to above is in the form of a member mounted on a support body for relative movement so as to be able to control the flow of gas through an associated orifice or passage. The member may be rapidly moved between the maximum and minimum flow conditions by a pulsed electrical current as discussed above.

In operation, the nature and arrangement of the closure member can be selected relative to other features such as the size of the associated orifice or passage, so as to provide a desired maximum rate of flow when in the fully open condition. When the closure member is closed, the flow through the device may be substantially zero (depending on the fluid leakage between valve and seat). To establish a flow between zero and the maximum, the closure member is repeatedly switched between the open and closed positions while accurately controlling the fraction of the total time for which the closure member is in the open position. Under such conditions, the flow through the valve body will consist of a pulsing fluid flow with the average flow equal to the maximum flow multiplied by the fraction of total time for which the valve member is in the open state. This is shown in FIGS. 2 and 3 and for this arrangement;

$$\text{average flow} = FMIN(B/A) + FMAX(A-B)/A$$

where B is the portion of a valve cycle during which flow is restricted and A is the cycle period It will be appreciated that any valve will take some time to move from a fully open position to a fully closed position and vice versa. During these transition periods the actual flow will not be accurately determinate. Various factors such as the closing and opening forces, and mass of valve closure member will vary the flow characteristics. The accuracy of the system will be enhanced if the times for which the valve remains open and closed are significantly longer than the time taken by the valve to move between the open and closed positions.

In some applications it is desirable that the flow is substantially smooth rather than pulsed. To achieve this it is necessary to provide means of averaging the flow and this can conveniently be achieved by one or more expansion chambers. However, the slower the pulse rate (period A in FIG. 2) the more difficult it is to achieve smooth flow, and also the longer the response time of the system to a change in setpoint. It is therefore preferred that the pulse rate be as fast as possible, and a pulse rate of about 27.5 Hz has been found satisfactory. Different pulse rates may be selected according to the requirements of the particular system.

Embodiments of the invention are described in detail in the following passages of the specification which refer to the accompanying drawings. The drawings, however, are merely illustrative of how the invention might be put into effect, so that the specific form and arrangement of the various features as shown is not to be understood as limiting on the invention.

Figure 1:
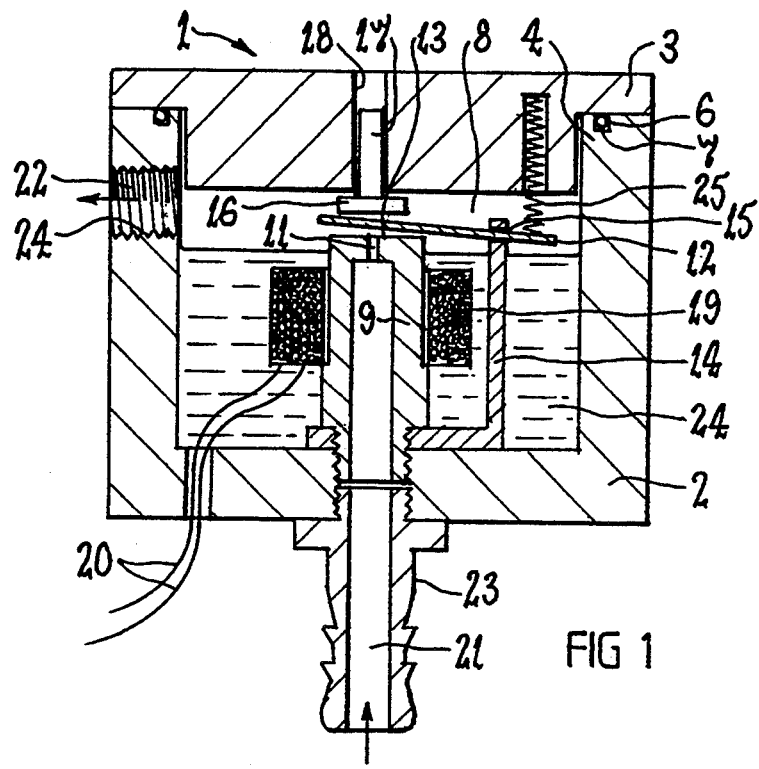
FIG. 1, is a diagrammatic cross-sectional view of one form of flow control valve which incorporates an embodiment of the invention.

The particular flow control device shown in FIG. 1 comprises a hollow housing 2 having a cap 3 fitted to an open upper end 4 of the housing 2. Preferably the cap 3 and the housing 2 are bolted together, but other securing means could be adopted, and the cap 3 fits into the upper end 4 of the housing 2. An O-ring seal 6 may be located in a groove 7 in the upper end 4 of the housing to provide a fluid tight seal between the housing 2 and the cap 3. The housing 2 and the cap 3 are preferably made from a non-magnetic material such as aluminium or plastics material. A chamber 8 is formed within the housing and a flow conduit 9 is mounted to the base 10 of the housing so as to project axially upwardly from the base 10. A restrictor 11 is formed at the upper end of the conduit 9 and the size of this restrictor 11 is selected to set the maximum flow rate through the device 1. This restriction 11 can be made so as to be adjustable but, for ease of construction, it is preferred that the size of the restrictor 11 is fixed and is determined by machining detail.

A valve closure member 12 is mounted within the chamber 8 so as to be movable towards and away from the end face 13 of the conduit 9. Preferably the valve closure member is pivotally connected to a yoke 14 through a pivotal connection 15 and is spring biased by means of a compression spring 25 into an open position, i.e. a position in which the valve closure member 12 allows maximum flow through the restrictor 11.

It is preferred that the conduit 9 and the valve member 12 are formed of a magnetic material and in this regard it is further preferred that these two components are made from a magnetic grade of stainless steel for corrosion resistance. Other materials might be suitable.

The valve member 12 in effect comprises an armature which is movable relative to the restrictor 11. It is preferably movable to a fully open position which is defined by an adjustable stop member 16 which is mounted in the end cap 3. The stop member 16 preferably includes a screw threaded shank 17 which is in cooperable engagement with a threaded bore 18 in the end cap 3. The bore 18 may be coaxial with the conduit 9 but that is not essential. The position of the stop member 16 can be varied by screwing the shank towards or away from the end face 13. The armature or valve member 12 is driven to its open position by suitable biasing means such as a compression spring 25, and is thus biased to a fully open position.

A coil 19 which is wound around the conduit 9 is adapted to create a magnetic field such as to attract the armature 12 against the end face 13 and thereby close the restrictor 11, when electrical current flows in the coil 19. For that purpose, the coil 19 is connected to a source of electrical current through conductor wires 20.

The device 1 has an inlet 21 connected to the tubular conduit 9 and an outlet 22, and flow rate of gas through the device 1 is controlled by movement of the valve member 12 towards and away from the restrictor 11. The inlet 21 is shown as a barbed fitting 23, although other arrangements are clearly possible. The gas outlet 22 is shown in this embodiment as a threaded bore 24, but any suitable outlet fitting may be connected to the outlet from the device 1.

As mentioned above, to close the flow passage through the device an electrical current is passed through the coil 19. This in turn sets up a magnetic flux which flows through the conduit 9, the yoke 14 and the armature 12 causing the armature 12 to be drawn against the end face 13 overcoming the force of the spring 25 and thereby closing the restrictor 11. In some arrangements, the armature 12 may not actually engage the end face 13, but nevertheless substantially obstructs gas flow through the restrictor 11.

To ensure that the gas flowing through the device does not come into contact with the driving coil 19 the coil may be potted (or encapsulated) with a suitable material as shown by numeral 24. Epoxy resin and injection moulded plastics have both proven to be suitable in practice, although it will be appreciated that other materials could also be suitable. The potting of the coil has the added benefit of increasing the rigidity of the overall structure. The connecting wires 20 are brought out of the housing below the level of the potting material 24 so that a fluid tight seal is maintained where the wires pass through the housing.

The gap between the end face 13 and the armature 12 when the armature is in its fully open position should preferably be large enough to ensure that the armature does not significantly contribute to the overall flow restriction. It has been determined theoretically and confirmed experimentally that such a condition is met when the gap between the end face 13 and the armature 12 is equal to or greater than ¼ of the diameter of the restrictor 11. Thus for a restrictor diameter of between 0.7 and 1.2 mm an armature movement of between 0.2 and 0.3 mm is sufficient. This total travel may be controlled by the adjustment of the adjustable stop 16.

An alternative mode of operation would be to intentionally limit the gap between the armature 12 and the end face 13 in the open position of the valve, so that the gap does produce some restriction to flow. The flow when the valve is in the open position will then be partially or totally determined by the size of the gap. Such an arrangement has the effect of making the maximum flow dependent on the gap setting, which in turn allows the maximum flow to be adjusted by changing the gap. Such an arrangement involving an adjustment facility may be of advantage in some applications.

Figure 2:
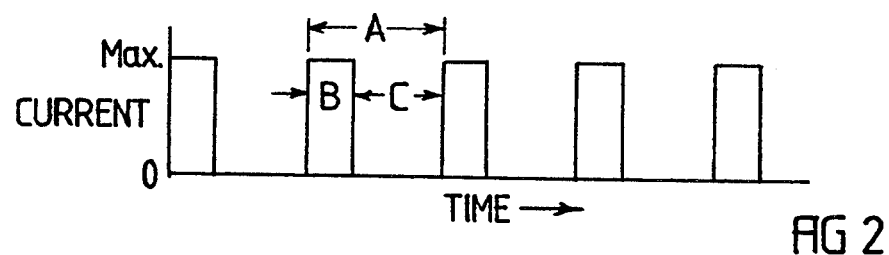
FIG. 2, is a graph representing a pulsed electrical signal used to control opening and closing of the valve shown in FIG. 1.
Figure 3:
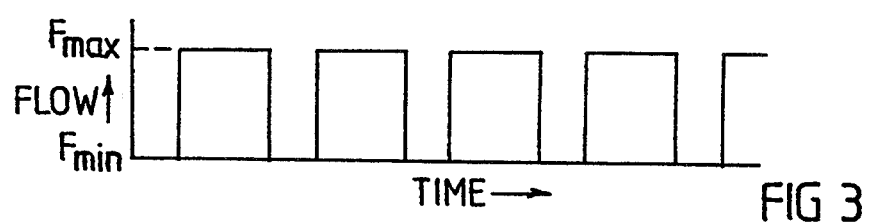
FIG. 3, is a graph representing the response of the valve of FIG. 1 to the pulsed signal represented by FIG. 2.

The coil 19 is driven by a pulsed electrical signal as shown graphically in FIG. 2 of the drawings. When electrical current is supplied (i.e. time period B) the armature 12 will be attracted against the end face 13 to close off or substantially restrict the flow of gas through the device. When electrical current is not supplied (i.e. time period C=A-B), the compression spring 25 will cause the armature 12 to move against the stop 16 allowing flow through the device to resume at the maximum rate.

In practice, it has been found that residual flux in the magnetic circuit can potentially hold the valve closed even when electrical power is removed. This effect can be overcome in a variety of ways, such as by incorporating a small air gap in the magnetic circuit, and such an air gap may be conveniently located between the armature 12 and the end face 13. Such an air gap might be achieved by positioning a section of suitable material between the armature 12 and the end face 13, and with proper selection of that material it could also serve to enhance the seal between the armature 12 and the end face 13 when the valve is in the closed position. In the particular valve under discussion, a material thickness of 0.05 to 0.2 mm has been found to be sufficient, and it has been convenient to achieve the gap by coating the armature 12 with polytetrafluoroethylene (PTFE), or by plating it with a non-magnetic material such a chromium. It will be appreciated however, that there are many other possible ways of achieving the air gap, if required.

As previously mentioned, the time of the time period A of a switching cycle can be selected according to requirements. If a pulsed flow is acceptable, the period A can be relatively long. For flow control of supply gas in spectrometers however, it is usually desirable to have substantially smooth or unpulsed flow, in which case rapid switching of the armature is desirable. It has been found that a pulse rate of between 20 and 50 Hz is satisfactory for reasonably steady flow with an optimum rate of about 27.5 Hz.

The severity of the pulse effect can be decreased by increasing the volume of the chamber 8. In the device depicted in FIG. 1 the chamber 8 is relatively small but this volume could be increased by increasing the size of the housing 2. The configuration of the various components will be selected with a view to the intended application of the device.

It is preferred that the armature 12 has a very low inertia in order to achieve the rapid switching times referred to above. It is further preferred that the switching time between fully closed and fully open position be in the order of 1 millisecond. With switching times of this order, the inductance of the coil 19 becomes a significant factor. This can have the effect of limiting the rate of rise of current which in turn increases the time taken for the valve to operate. A technique which may be adopted to overcome inductance effects is to insert a resistor in series with the coil 19 and drive the combination from a high voltage. Since the time constant of the coil is given by the formula:

$$\text{time constant} = \text{inductance/resistance},$$

increasing the resistance reduces the time constant and thus increases the rate of rise of current. This approach has the limitation that the power dissipation is also increased and in the present application power dissipation in this manner becomes excessive. The problem may be overcome by driving the system from a dual electrical supply facility. At the time the coil 19 is energised, a high voltage is switched on to cause a rapid increase of current through the coil 19. Once the current has reached a sufficient level to drive the armature 12, the supply voltage is reduced to a level which is just enough to maintain the current flow. Such an approach achieves rapid operation without heat dissipation problems. Any suitable regulating means may be adopted to cause the changeover between the two voltage supplies. The drive voltage variation and the resulting valve operation are shown graphically in FIGS. 4 and 5 respectively.

Figure 4:
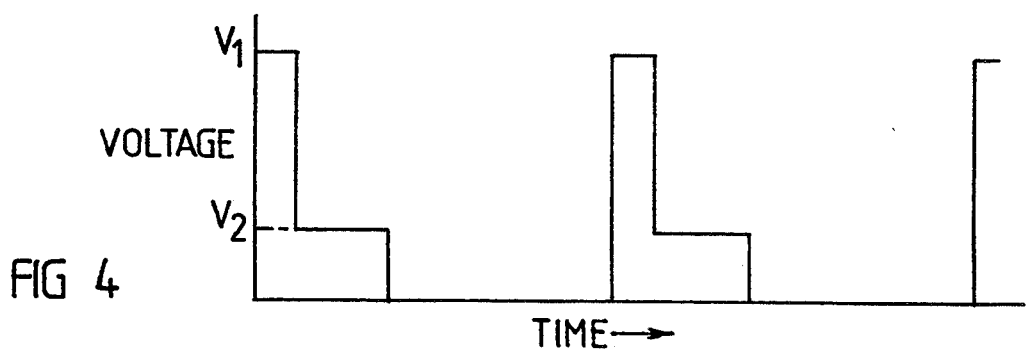
FIG. 4, is a graph representing a variation in voltage supply during the generation of each pulse represented by FIG. 2, but in which the time periods are shown on a different seal to that of FIGS. 2 and 3.
Figure 5:
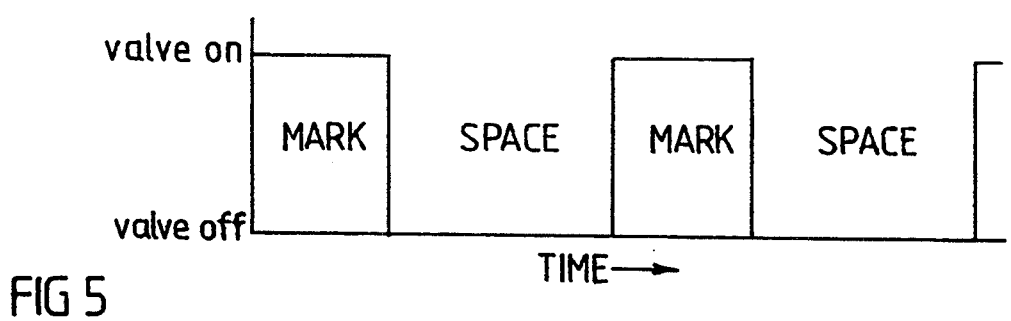
FIG. 5 is a graphical representation of the mark/space signal from a processor which controls the valve so as to produce the pulse frequency and duration represented by FIG. 4.

In the FIG. 4 arrangement, the high voltage V1 is maintained for a suitable period of time—e.g., 2 milliseconds—and the voltage is then dropped to a relatively low holding voltage V2. The voltage V2 is sustained for the duration of the pulse. The time span of each mark/space cycle as depicted by FIG. 5 will be selected to suit requirements, and a time span of 37 milliseconds has been used in practice.

Figure 6:
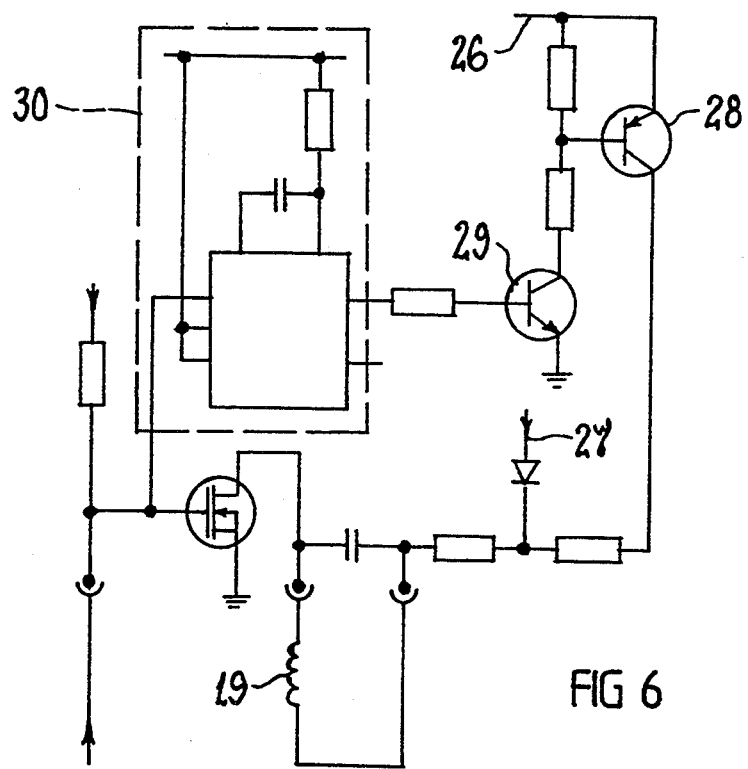
FIG. 6 is a representation of one form of circuit for achieving the voltage change diagrammatically represented by FIG. 4.

An alternative arrangement would be to drive the coil 19 from a constant current supply source which would have the effect of automatically adjusting the supply voltage. This could be made similarly efficient by employing switching regulator techniques, but a dual supply system as described above is generally preferred. One possible electric circuit capable of implementing the described dual voltage configuration is shown in FIG. 6. However, it should be understood that there are many other possible configurations capable of achieving the same effect.

In the FIG. 6 circuit, high and low voltage supplies 26 and 27 respectively are connectable to the coil 19 through switches 28 and 29 which are under the control of a regulator 30, such as a mono-stable circuit. The FIG. 6 circuit operates in a known manner and requires no further explanation.

Figure 7:
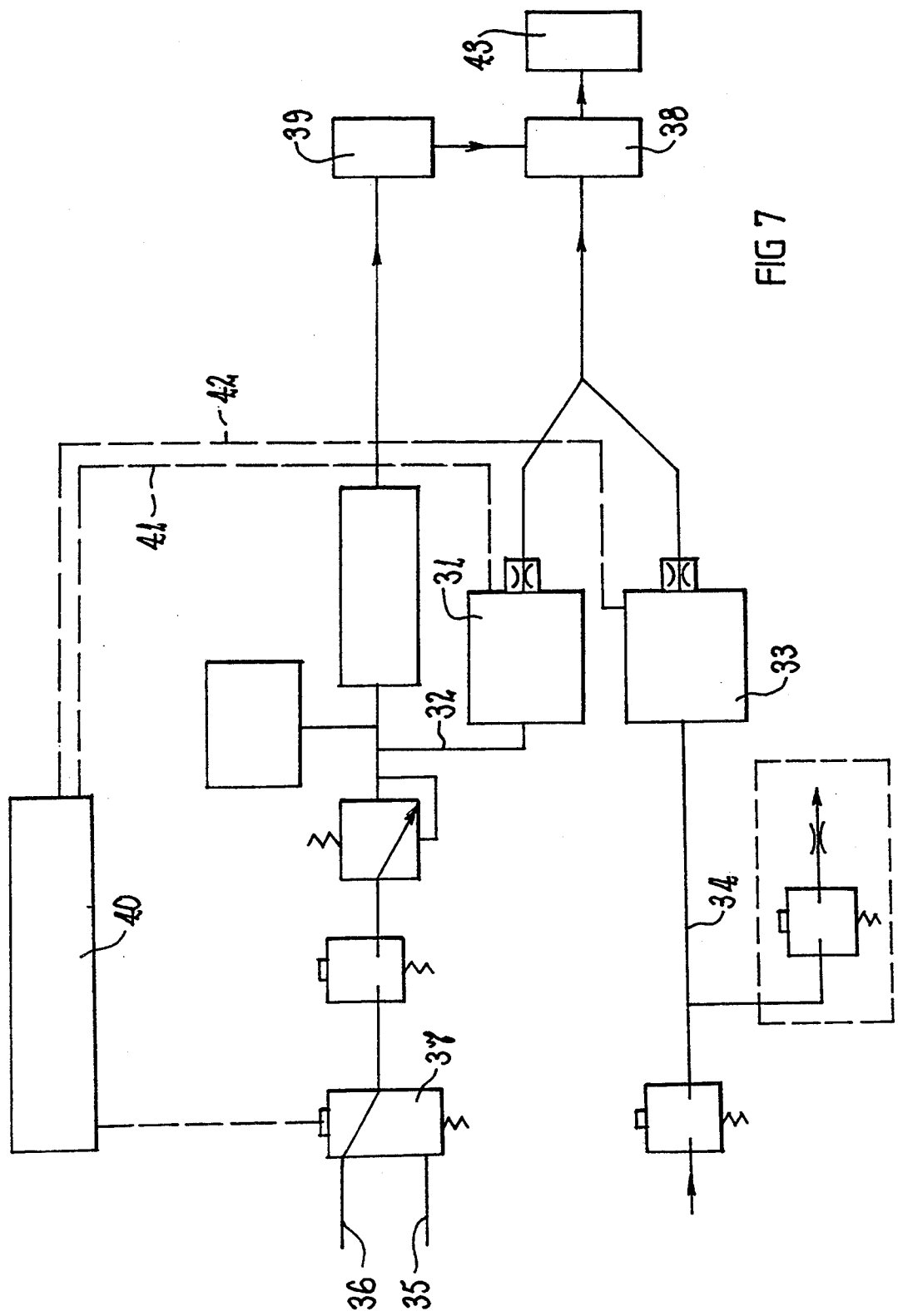
FIG. 7 is a diagrammatic representation of a spectrometer incorporating a flow control device according to the invention.

A flow control device as described is particularly suited for use in an AA spectrometer for control of the flow rate of supply gas to the burner. In an AA spectrometer of the type depicted diagrammatically in FIG. 7 there will preferably be two flow control devices. One device 31 controls flow through the oxidant supply line 32, and the other device 33 controls flow through the fuel supply line 34. Two types of oxidant may be available as shown in FIG. 7. For example one oxidant may be nitrous oxide supplied through line 35, and the other may be air supplied through line 36. A change over valve 37 controls which oxidant is supplied at any one time. Oxidant is shown supplied to a spray chamber 38 both directly and by way of a nebulizer or atomizer 39, and the spray chamber 38 is connected to a burner 43 as shown. A microprocessor 40 is connected to the change over valve 37 so as to control selection of an appropriate oxidant supply 35 or 36.

The flow rates of the gases supplied to the burner 38 by way of the oxidant line 32 and fuel line 34 are controlled by flow control devices 31 and 33 respectively. Each of the flow control devices 31 and 33 may be constructed as depicted in FIG. 1, or could be of any other suitable construction. The mark to space ratio of the current supplied to each of flow control devices 31 and 33 is controlled by the microprocessor 40 through connections 41 and 42 respectively.

The flow rates of fuel and oxidant supplied to the burner 38 are controlled by the microprocessor 40 establishing the waveform of electrical current supplied to each of the flow control devices 31 and 33. Clearly, the mark to space ratio of the electrical current waveform can be varied very rapidly, using the microprocessor 40 or any other suitable means. A flow control device as described is ideally adapted to be controlled by digital control means.

Because the relationship between pressure drop across a restrictor and flow rate through the restrictor is very predictable and reproducable, the two flow control device 31 and 33 can be run on an open loop control arrangement. This eliminates the need for a flow rate sensor and feedback loop. Thus, since the feedback loop is eliminated, processing time of the microprocessor 40 is reduced. The microprocessor 40 is used only for setting the flow of fuel and oxidant, and is not required to monitor that flow.

Many variations may be made to the above described components and arrangements of parts without departing from the spirit or ambit of the invention as defined by the appended claims.

Having now described my invention, what I claim as new and desire to secure by Letters Patent is:

1. In an optical spectrometer gas supply flow control system, the method of controlling flow of said supply gas to an atomizer of said spectrometer comprising, using an open loop flow control technique employing the steps of:

(a) providing a fixed pressure head to an electric valve for forcing said supply gas through said electric valve;

(b) switching said valve between a maximum open position and a minimum open position in response to a pulsed electrical signal provided to said valve, said pulsed electrical signal having a space time and a mark time wherein said space time corresponds to the time in which said valve is in said maximum open position and said mark time corresponds to the time in which said valve is in said minimum open position;

(c) controlling the ratio of mark to space time to control the average flow rate through said valve wherein said average flow rate equals Fmin (B/A)+Fmax ((A-B)/A) where Fmax is maximum flow and Fmin is minimum flow, and where B is mark time and A-B is space time and A equals the total of mark time plus space time.

2. The method of claim 1 wherein said pulsed electrical signal coinciding with said mark comprises an initial high voltage portion and a final lower voltage portion.

3. The method of claim 2 wherein said pulsed electrical signal coinciding with said space comprises a voltage having a value lower than said final lower voltage portion of said mark signal and wherein said electric valve utilizes a spring to return to said maximum open position.

4. An optical spectrometer supply gas flow controller comprising:

(a) an electrical operable valve for passing said supply gas;

(b) means to provide a pressurized supply gas to said electric valve under fixed pressure;

(c) means to cause said electrically operable valve to switch responsive to electric pulses only between full open position and full closed position;

(d) pulse controller means to provide said electric pulses, said pulses having a mark off time and space on time, and whereby the flow rate of said supply gas through said electric valve is proportional to the ratio of said space on time to said space on time plus said mark off time, wherein said space on time corresponds to the time in which said valve is in said full open position and said mark off time corresponds to the time in which said valve is in said full closed position.

5. The apparatus of claim 4 wherein said pulse controller means includes means for causing said electric pulse during said mark time to have an initial high voltage and a low final voltage.

6. The apparatus of claim 5 wherein said pulse controller has means to switch to a first high voltage power supply to provide said initial high voltage and to switch to a second low voltage supply to provide said low final voltage.

7. The apparatus of claim 4 wherein said electrically operable valve comprises:

(a) an electric coil having a conduit for carrying said gas axially aligned therewith, said electric coil being connected to said pulse controller;

(b) a closure member, said closure member being positioned with respect to said conduit for closing said conduit when a current pulse is flowing in said coil; and (c) a magnetic circuit closing a flux path around said coil, said magnetic circuit including an air gap when said closure member closes said conduit, said air gap being a means for lowering the residual flux in said magnetic circuit.

8. A new method of using an electrically operable valve comprising;

(a) inserting said electrically operable valve in a conduit between a pressure source of gas and an optical spectrometer atomizer, said valve having a fully open position and a fully closed position; and (b) controlling the flow rate of said gas in said conduit by adjustably controlling the duty cycle ratio of said electrically operable valve, where said duty cycle is the ratio of time in fully open position to the sum of the time in the fully open plus fully closed positions.

* * * * *